US011566185B1

(12) United States Patent
Koseoglu et al.

(10) Patent No.: US 11,566,185 B1
(45) Date of Patent: Jan. 31, 2023

(54) METHODS AND CATALYSTS FOR CRACKING HYDROCARBON OIL

(71) Applicants: Saudi Arabian Oil Company, Dhahran (SA); JGC Catalysts and Chemicals Ltd., Kawasaki (JP); Japan Cooperation Center Petroleum, Tokyo (JP)

(72) Inventors: Omer Refa Koseoglu, Dhahran (SA); Yaming Jin, Dhahran (SA); Tatsuaki Hasegawa, Kitakyushu (JP); Takaki Mizuno, Kitakyushu (JP); Naoyuki Kido, Kitakyushu (JP); Seiji Arakawa, Kitakyushu (JP)

(73) Assignees: Saudi Arabian Oil Company, Dhahran (SA); JGC Catalysts and Chemical Ltd., Kawasaki (JP); Japan Cooperation Center Petroleum, Tokyo (JP)

(*) Notice: Subject to any disclaimer, the term of this patent is extended or adjusted under 35 U.S.C. 154(b) by 0 days.

(21) Appl. No.: 17/825,247

(22) Filed: May 26, 2022

(51) Int. Cl.
| | |
|---|---|
| C10G 11/05 | (2006.01) |
| C10G 11/18 | (2006.01) |
| B01J 29/16 | (2006.01) |
| C07C 4/06 | (2006.01) |

(52) U.S. Cl.
CPC ............. *C10G 11/05* (2013.01); *B01J 29/166* (2013.01); *C07C 4/06* (2013.01); *C10G 11/18* (2013.01); *C07C 2523/34* (2013.01); *C07C 2529/16* (2013.01); *C10G 2300/202* (2013.01); *C10G 2300/308* (2013.01); *C10G 2400/02* (2013.01); *C10G 2400/20* (2013.01)

(58) Field of Classification Search
CPC ................... C10G 11/05; C10G 11/18; C10G 2300/202; C10G 2300/308; C10G 2400/02; C10G 2400/20; B01J 29/166; C07C 4/06; C07C 2523/34; C07C 2529/16
See application file for complete search history.

(56) References Cited

U.S. PATENT DOCUMENTS

| | | |
|---|---|---|
| 4,437,978 A | 3/1984 | Chester et al. |
| 5,641,395 A | 6/1997 | Hettinger, Jr. et al. |
| 6,069,106 A | 5/2000 | Hettiner, Jr. |
| 6,535,632 B1 | 3/2003 | Park et al. |
| 6,635,168 B2 | 10/2003 | Zhao et al. |
| 6,884,744 B2 | 4/2005 | Cheng et al. |
| 10,357,761 B2* | 7/2019 | Koseoglu ................ C01B 39/24 |
| 11,078,431 B2 | 8/2021 | Koseoglu et al. |
| 11,098,256 B2 | 8/2021 | Koseoglu et al. |

(Continued)

*Primary Examiner* — Thuan D Dang
(74) *Attorney, Agent, or Firm* — Dinsmore & Shohl LLP

(57) ABSTRACT

According to one or more embodiments described herein, a method for cracking a hydrocarbon oil may include contacting the hydrocarbon oil with a fluidized cracking catalyst including an ultra-stable Y-type zeolite in a fluidized catalytic cracking unit to produce light olefins, gasoline fuel, and coke. At least 99 wt. % of the hydrocarbon oil may have a boiling point greater than 350° C. The ultra-stable Y-type zeolite may be a framework-substituted zeolite in which a part of aluminum atoms constituting a zeolite framework thereof is substituted with 0.1-5 mass % zirconium atoms and 0.1-5 mass % titanium ions on an oxide basis. The fluidized cracking catalyst may include from 3.5 wt. % to 10 wt. % of one or more Group 7 metal oxides.

18 Claims, 2 Drawing Sheets

(56) References Cited

U.S. PATENT DOCUMENTS

| | | |
|---|---|---|
| 2002/0179492 A1 | 12/2002 | Zhao et al. |
| 2003/0013601 A1 | 1/2003 | Cheng et al. |
| 2008/0308456 A1 | 12/2008 | Stamieres et al. |
| 2011/0052467 A1 | 3/2011 | Chase et al. |
| 2016/0288107 A1 | 10/2016 | Kilmartin et al. |
| 2022/0001362 A1 | 1/2022 | Koseoglu et al. |

* cited by examiner

METHODS AND CATALYSTS FOR CRACKING HYDROCARBON OIL

BACKGROUND

Field

The present disclosure relates to catalytic cracking and, more specifically, to catalyst for catalytic cracking and methods for the uses thereof.

Technical Background

In fluidized catalytic cracking (FCC) processes, petroleum derived hydrocarbons are catalytically cracked with a catalyst maintained in a fluidized state, which is regenerated on a continuous basis. The main product from such processes has generally been gasoline. Other products are also produced in smaller quantities via FCC processes such as liquid petroleum gas and cracked gas oil.

SUMMARY

Generally, coke is a byproduct of the FCC process. Coke may be deposited on the catalyst during the cracking reaction, and the coke may be burned off during regeneration of the catalyst. Burning the coke during regeneration of the catalyst may provide heat for the cracking reaction. However, some feedstocks to the FCC process, such as hydrotreated feedstocks, are low in coke precursors, and the amount of coke produced by cracking those feedstocks may be insufficient to maintain the overall heat balance of the FCC process when the coke is burned during catalyst regeneration. Accordingly, there is a need for catalysts that produce sufficient coke, such that burning the coke during regeneration of the catalyst provides enough heat to drive the cracking reaction and maintain the heat balance of the FCC process.

As described in the present disclosure, a fluidized cracking catalyst including a Group 7 metal may have a good cracking activity while producing sufficient coke to maintain the overall heat balance of the FCC process when the coke is burned during catalyst regeneration. Generally, coke may be formed by the condensation or polymerization reaction of aromatic molecules in the feedstock. Certain feedstocks, such as hydrotreated feedstocks, may be low in these coke precursors. For example, hydrocracking or hydrotreating a feedstock may result in a feedstock including fewer polyaromatic molecules, which may reduce the amount of coke formed during the cracking reaction. If the production of coke during the cracking reaction is too low, there may be insufficient coke deposited on the catalyst to maintain the heat balance of the FCC process when the coke is burned during regeneration of the catalyst. The inclusion of a Group 7 metal in the fluidized cracking catalyst may promote the formation of coke from feedstocks that are low in coke precursors. This may result in sufficient heat being generated by burning the coke during the regeneration of the catalyst to maintain the heat balance of the FCC process, or to at least reduce the need for supplemental heat sources.

According to one or more embodiments described herein, a method for cracking a hydrocarbon oil may include contacting the hydrocarbon oil with a fluidized cracking catalyst comprising an ultra-stable Y-type zeolite in a fluidized catalytic cracking unit to produce light olefins, gasoline fuel, and coke. At least 99 wt. % of the hydrocarbon oil may have a boiling point greater than 350° C. The ultra-stable Y-type zeolite may be a framework-substituted zeolite in which a part of aluminum atoms constituting a zeolite framework thereof is substituted with 0.1-5 mass % zirconium atoms and 0.1-5 mass % titanium ions on an oxide basis. The fluidized cracking catalyst may comprise from 3.5 wt. % to 10 wt. % of one or more Group 7 metal oxides.

Additional features and advantages of embodiments of the present disclosure will be set forth in the detailed description that follows, and in part will be readily apparent to a person of ordinary skill in the art from the description or recognized by practicing the technology as described in this disclosure, including the detailed description that follows and the claims.

BRIEF DESCRIPTION OF THE DRAWINGS

The following detailed description of embodiments of the present disclosure can be best understood when read in conjunction with the following drawing in which.

Figure 1:
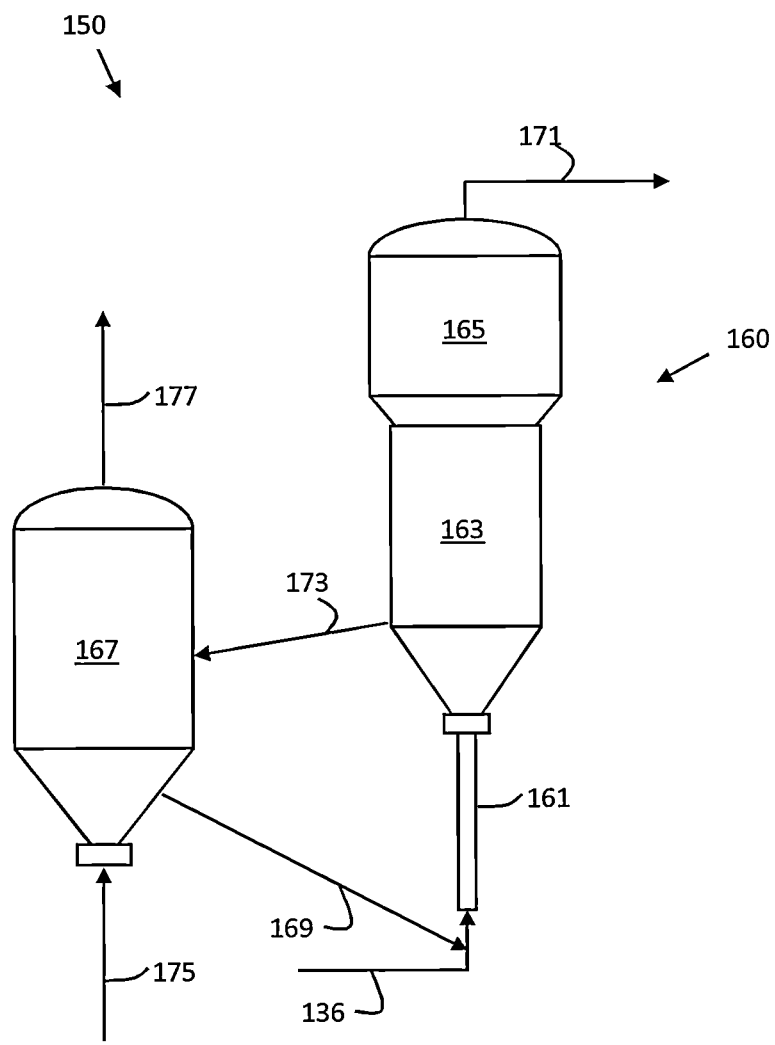
FIG. 1 is a schematic diagram of a riser fluidized catalytic cracking unit, according to one or more embodiments described herein.
Figure 2:
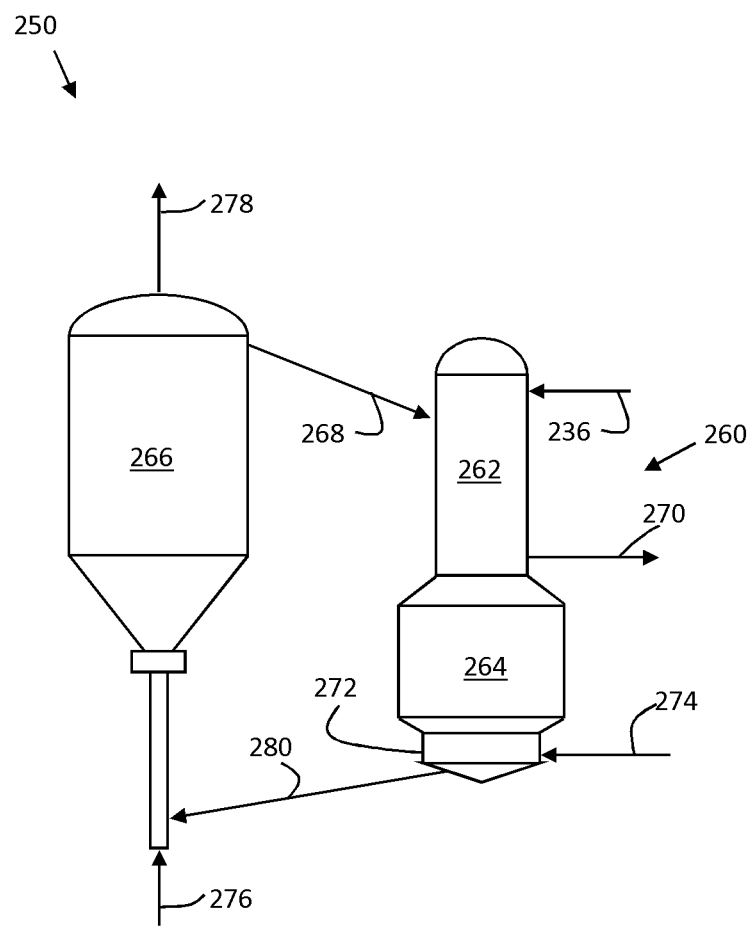
FIG. 2 is a schematic diagram of a downflow fluidized catalytic cracking unit, according to one or more embodiments described herein.

For the purpose of describing the simplified schematic depiction of FIGS. 1 and 2, the numerous valves, temperature sensors, electronic controllers, and the like, that may be employed and well known to a person of ordinary skill in the art are not included. It should be understood that these components are within the spirit and scope of the present disclosure. However, operational components, such as those described in the present disclosure, may be added to the embodiments described in the present disclosure.

It is noted that arrows in the drawing refer to process streams. However, the arrows may equivalently refer to transfer lines, which may serve to transfer process streams between two or more system components. Additionally, arrows that connect to system components may define inlets or outlets in each given system component. The arrow direction corresponds generally with the major direction of movement of the materials of the stream contained within the physical transfer line signified by the arrow. Furthermore, arrows that do not connect two or more system components may signify an outlet stream that exits the depicted system or an inlet stream that enters the depicted system.

It is further noted that arrows in the drawing may schematically depict process steps of transporting a stream from one system component to another system component. For example, an arrow from one system component pointing to another system component may represent "passing" a process stream from one system component to another system component, which may include the contents of a process stream "exiting" or being "removed" from one system component and "introducing" the contents of that product stream to another system component.

Reference will now be made in greater detail to various embodiments, some embodiments of which are illustrated in the accompanying drawing.

DETAILED DESCRIPTION

Described herein are catalysts (sometimes referred to as "catalyst compositions" or "fluidized cracking catalysts") useful for cracking hydrocarbon oils, and methods for using such catalysts to crack hydrocarbon oils. As is described herein, the fluidized cracking catalysts may include ultra-stable Y-type zeolite that is framework-substituted zeolite in which a part of aluminum atoms constituting the zeolite framework thereof is substituted with zirconium atoms and titanium ions. As is described herein, the incorporation of a Group 7 metal oxide in the fluidized cracking catalysts increases coke formation, which may be desirable in some chemical processes.

In one or more embodiments, the fluidized cracking catalyst is useful to converting hydrocarbon oils having a composition where at least 99 wt. % of the hydrocarbon oil has a boiling point greater than 350° C. Hydrocarbon oils that boil at such temperatures may be referred to herein as heavy hydrocarbons. As used herein, "heavy hydrocarbons" include common refinery streams such as vacuum gas oil (VGO), hydrocracking unit unconverted bottoms or recycle oil, deasphalted oil (DAO) obtained from a solvent deasphalting process, demetallized oil, light or heavy coker gas oil obtained from a coker process, cycle oil obtained from a separate fluidized catalytic cracking process or recycled from an FCC process using the present catalyst, gas oil obtained from a visbreaking process, or combinations comprising at least one of the foregoing sources or hydrogenated derivatives of the oils.

According to embodiments described herein, the catalyst compositions are used alone or in effective combination with one or more additional fluidized cracking catalyst materials that are known or become known for fluidized catalytic cracking processes, to thereby form a catalyst mixture suitable for fluid catalyst cracking operations. In some embodiments particularly to enhance production of propylene or lighter olefins and gasoline while reducing the production of dry gas.

The fluidized cracking catalyst for use FCC operations for conversion of heavy hydrocarbons provided herein comprises a framework-substituted zeolite that contains zirconium atoms partially constituting a framework of an ultra-stable Y-type zeolite ("USY"). The framework-substituted zeolite may be a USY-type zeolite in which silicon atoms and aluminum atoms form a zeolite framework and in which a portion of the aluminum atoms forming a zeolite framework is substituted with zirconium atoms.

As used herein, USY-type zeolite in which a portion of the aluminum atoms forming a zeolite framework is substituted with zirconium atoms is referred to as "framework-substituted zeolite." Further, framework-substituted zeolite in which a part of aluminum atoms forming a zeolite framework is substituted only with zirconium atoms is referred to as a "zirconium-substituted zeolite" or "Zr-USY," Zirconium atoms which are substituted for the aluminum atoms forming a framework of the ultra-stable Y-type zeolite serve as constituents of the framework of the ultra-stable Y-type zeolite. In the framework-substituted zeolite described herein, a portion of zirconium atoms can optionally be carried on or combined with inner surfaces of pores, for instance, in the form of metal oxides, i.e., zirconium oxide particles. The metal oxides of zirconium are combined with inner surfaces of mesopores of the USY zeolite. The zeolite having a high mesopore volume may be prepared by bringing a framework substituted zeolite into contact with a strongly acidic aqueous solution at a pH of 0.8 up to and including 2, drying the zeolite at a temperature in the range of 50° C. to 200° C., and firing the dry zeolite at 350° C. to 600° C., to prepare a zeolite in which metal oxide ultrafine particles are combined with (also referred to as "carried on") inner surfaces of pores. The procedure is described in more detail in Japanese Unexamined Patent Application Publication No. 2002-255537, which is incorporated herein by reference.

In one or more embodiments, the framework substitution can be verified by, for example, X-ray fluorescence, high frequency plasma emission spectrometry, atomic absorption spectrometry, ultraviolet-visible-near-infrared spectrophotometry (UV-Vis-NIR), Fourier transform infrared spectroscopy (FT-IR), or nuclear magnetic resonance spectrometry (NMR). Note that in the framework-substituted zeolite in which the framework of a β-zeolite is substituted by zirconium atoms, it is known that a UV spectrum indicating the presence of zirconium atoms is shown in the range of 200 nanometers (nm) to 220 nm (for example, see FIG. 3 in Rakshe, Bhavana, Veda Ramaswamy and Arumugamangalam Venkataraman Ramaswamy. "Acidity and m-Xylene Isomerization Activity of Large Pore, Zirconium-Containing Alumino-silicate with BEA Structure." *Journal of Catalysis* 188 (1999): 252-260.

In one or more embodiments, the framework-substituted zeolite described herein generally contains zirconium atoms in the range of 0.1% to 5%. In some embodiments 0.2% to 4%, and in further embodiments 0.3% to 3%, as a mass percentage of in terms of zirconium oxide (i.e., $ZrO_2$), based on the framework-substituted zeolite. In this regard, a content range (based on oxides) of zirconium atoms includes all of the contents of zirconium atoms substituted for aluminum atoms forming a zeolite framework and zirconium atoms which are not substituted for the aluminum atoms, e.g., carried on inner surfaces of the pores of the framework-substituted zeolite.

In some embodiments, it is believed that the zirconium content of the framework-substituted zeolite of less than 0.1% by mass in terms of oxide based on a mass of the framework-substituted zeolite does not result in an effective amount of a solid acid for FCC reactions of hydrocarbon oil. Similarly, a zirconium atom content exceeding 5% by mass in terms of oxide based on the mass of the framework-substituted zeolite-1 does not result in an effective pore volume for FCC reactions of hydrocarbon oil, and it is thus prone to reduce the catalytic activity.

In additional embodiments of the zirconium-substituted zeolite, framework substitutions of titanium atoms can be provided for a portion of the aluminum atoms forming the zeolite framework. In these embodiments, titanium atoms can be contained in the framework-substituted zeolite-1 in a proportion in the range of 0.1% to 5%, in some embodiments 0.5% to 4%, and in further embodiments 0.6% to 3%, as a mass percentage of in terms of titanium oxide (i.e., $TiO_2$), based on the framework-substituted zeolite.

In one or more embodiment, in this regard, if a content of the above titanium atoms in the framework-substituted zeolite is less than 0.1% by mass in terms of oxide, an amount of a solid acid which is effective for a fluidized catalytic cracking reactor is not obtained when a catalyst prepared by using the above framework-substituted zeolite as a support is applied to a fluidized catalytic cracking reactor, and therefore an activity of hydrocarbon oil in a fluidized catalytic cracking reactor tends to be reduced. Similarly, if a content of titanium atoms in the framework-substituted zeolite exceeds 5% by mass in terms of oxide, a pore volume which is effective for a fluidized catalytic cracking reactor is not obtained when a catalyst prepared by using the above framework-substituted zeolite as a support is applied to a fluidized catalytic cracking reactor, and therefore an activity of hydrocarbon oil in a fluidized catalytic cracking reactor tends to be reduced. A content of titanium atoms in the framework-substituted zeolite can be measured by, for example, an X-ray fluorescence analyzer, a high frequency plasma emission spectrometer, an atomic absorption spectrometer or the like.

In one or more embodiments, the fluidized cracking catalyst including the framework-substituted zeolite may comprise one or more Group 7 metal oxides. As described herein, Group 7 elements refer to those under IUPAC nomenclature, and include manganese (Mn), technetium (Tc), rhenium (Re), and bohrium (Bh). Any degree of oxidation of these Group 7 elements in contemplated, including MnOx, TcOx, ReOx, and BhOx, where x is from 1 to 3. The fluidized cracking catalyst may include a single Group 7 metal oxide or multiple Group 7 metals oxides, in any combination.

Without intending to be bound by theory, the inclusion of Group 7 metal oxides in the fluidized cracking catalyst may enhance the coke making characteristics of the catalyst. This may be beneficial when cracking feedstocks that are low in coke precursors. Certain feedstocks, such as hydrotreated feedstocks, may be low in these coke precursors. For example, hydrocracking or hydrogenation may result in fewer polyaromatic molecules in the feedstock, which may reduce the amount of coke formed during the cracking reaction. If an insufficient amount of coke is formed during the cracking reaction, then burning the coke during regeneration of the catalyst may result in insufficient heat to maintain the heat balance of the FCC process. However, including a Group 7 metal in the catalyst may increase the coke produced during the cracking reaction, even when cracking feedstocks that are low in coke precursors. This may result in sufficient coke to maintain the heat balance of FCC process when the coke is burned during catalyst regeneration.

According to embodiments, the fluidized cracking catalyst may include from 3.5 wt. % to 10 wt. % of Group 7 metal oxides (that is, if more than one Group 7 metal oxide is present, the total wt. % of all Group 7 metal oxides is from 3.5 wt. % to 10 wt. %. For example, the total wt. % of all Group 7 metal oxides may be from 3.5 wt. % to 4 wt. %, from 4 wt. % to 4.5 wt. %, from 4.5 wt. % to 5 wt. %, from 5 wt. % to 5.5 wt. %, from 5.5 wt. % to 6 wt. %, from 6 wt. % to 6.5 wt. %, from 6.5 wt. % to 7 wt. %, from 7 wt. % to 7.5 wt. %, from 7.5 wt. % to 8 wt. %, from 8 wt. % to 8.5 wt. %, from 8.5 wt. % to 9 wt. %, from 9 wt. % to 9.5 wt. %, from 9.5 wt % to 10 wt. %, or any combination of these ranges. Without intending to be bound by theory, if the amount of the Group 7 metal oxides in the fluidized cracking catalyst is less than 3.5 wt. %, then the effect of coke formation is diminished. If the amount of Group 7 metal oxides in the fluidized cracking catalyst is greater than 10 wt. %, then the fluidized cracking catalyst may have a reduced cracking activity due to a reduced amount of components that promote cracking, such as zeolite and active alumina.

Certain ranges of crystal lattice constant, specific surface area, and silica-alumina ratio are provided for the framework-substituted zeolite. In the fluidized catalytic cracking catalyst for hydrocarbon oil according to the present disclosure, a specific surface area thereof falls, in some embodiments, in a range of 200 to 450 m$^2$/g, and a total volume of pores by nitrogen adsorption falls in a range of 0.1 to 0.75 ml/g.

According to one or more embodiments, the framework-substituted zeolite materials herein may have a crystal lattice constant in the range of 2.430 nm to 2.450 nm, and in some embodiments, in the range of 2.435 nm to 2.445 nm. A crystal lattice constant of framework-substituted zeolite of less than 2.430 nm tends to reduce the activity of the FCC catalyst using the respective framework-substituted zeolites as supports because of a high $SiO_2/Al_2O_3$ molar ratio in the framework structure, and a small number of solid acid sites serving as active sites for the hydrocarbon cracking. A crystal lattice constant of the framework-substituted zeolite exceeding 2.450 nm results in breakage of the crystal structure of the framework-substituted zeolite during FCC reactions because of low heat resistance, and tends to cause a reduction in the activity of the FCC catalyst using the respective framework-substituted zeolites as supports.

The crystal lattice constant can be measured by reference to ASTM method D3942. X-ray diffraction peaks from the (533) and (642) planes of Y zeolite are measured using silicon (Si) serving as a primary reference material and using titanium oxide (anatase) serving as a secondary reference material.

The framework-substituted zeolite described herein may possess a specific surface area in the range of 600 m$^2$/g to 900 m$^2$/g, and in some embodiments, 650 m$^2$/g to 800 m$^2$/g. This specific surface area is a value determined by the BET (Brunauer-Emmett-Teller) method using nitrogen adsorption. A specific surface area of the framework-substituted zeolite of less than 600 m$^2$/g potentially reduces the number of effective solid acid sites in the FCC reaction. A specific surface area exceeding 900 m$^2$/g is, at the time of filing the instant application, impractical due to production limitations, however it is contemplated that advantages can be found if developments in processing the zeolite material are discovered.

The framework-substituted zeolites described herein may generally have a molar ratio of $SiO_2$ to $Al_2O_3$ (silica-alumina ratio) generally in the range of 5:1 to 100:1, in some embodiments 20:1 to 100:1, and in additional embodiments 10:1 to 80:1. A silica-alumina ratio of less than 20, and in some embodiments less than 5, does not result in an effective pore volume and is thus liable to cause a reduction in activity in cracking reactions. A silica-alumina ratio of the framework-substituted zeolite exceeding 100 tends to cause a reduction in cracking activity due to a reduced number of solid acid sites.

According to embodiments, to produce the presently disclosed framework-substituted zeolite, a portion of the aluminum atoms within the USY zeolite framework are substituted with zirconium atoms, and USY zeolite is further treated to substitute part of the aluminum atoms within the framework with titanium atoms. The disclosure of WO 2012/018819, which is incorporated herein by reference, describes a similar catalyst composition useful for hydrotreating operations, and the same synthesis procedures can be followed. Following this preparation, a Group 7 metal oxide may be incorporated by mixing the Group 7 metal oxide with the zeolite in a slurry mixture and spray-drying the slurry mixture. It is noted that the present examples provide details on such a process, but that the presently described catalyst are not limited by synthesis technique, and other synthesis techniques are contemplated to be acceptable.

In some embodiments, a framework-substituted zeolite is produced by firing an ultra-stable Y-type zeolite at 500° C. to 700° C., the ultra-stable Y-type zeolite having a crystal lattice constant of 2.430 to 2.450 nm, a specific surface area of 600 to 900 m$^2$/g, and a molar ratio of $SiO_2$ to $Al_2O_3$ generally in the range of 5:1 to 100:1, in some embodiments 20:1 to 100:1, and in additional embodiments 25:1 to 80:1. A suspension may be formed containing the fired ultra-stable Y-type zeolite, the suspension having a liquid/solid mass ratio of 5 up to and including 15. An inorganic acid or an organic acid is added so that a pH of the suspension is 1.0 to 2.0. Subsequently, a solution containing a zirconium compound may be mixed. The solution is neutralized with, for example, an aqueous ammonia, so that the pH is 7.

Ultra stable Y-type zeolite is used a raw material in one or more embodiments of methods for manufacturing the herein framework-substituted zeolite. Production methods for ultra-stable Y-type zeolite are known to a person having ordinary skill in the art. The ultra-stable Y-type zeolite used in the embodiments of manufacturing methods described herein may generally be zeolite having a crystal lattice constant (UD) in the range of 2.430 to 2.450 nm, a specific surface area of 600 to 900 m$^2$/g, and a molar ratio of SiO$_2$ to Al$_2$O$_3$ generally in the range of 5:1 to 100:1, in some embodiments 20:1 to 100:1, and in additional embodiments 10:1 to 80:1.

For example, in one production method for the above-described ultra-stable Y-type zeolite, a Y-type zeolite (Na—Y) synthesized by a common method is subjected to the exchange of sodium ions with ammonium ions by a conventional method, for example: dispersing Y-type zeolite in water to prepare a suspension, adding ammonium sulfate thereto, washing the solid matter with water, washing it with an ammonium sulfate aqueous solution at temperature in the range of 40° C. to 80° C., subsequently washing it with water at temperature in the range of 40° C. to 95° C., and drying at 100° C. to 180° C. for 30 minutes. Accordingly an ammonium-exchanged Y-type zeolite, $NH_4$—$^{50\ to\ 70}Y$ in which 50 wt. % to 70 wt. % of Na contained in the Y-type zeolite is substituted with $NH_4$. Subsequently, a hydrogen type Y-type zeolite (HY) may be prepared by calcining the above ammonium-exchanged Y-type zeolite ($NH_4$—$^{50\ to\ 70}Y$) at 500° C. to 800° C. for 10 minutes to 10 hours in, for example, a saturated vapor atmosphere. Then, an ammonium-exchanged Y-type zeolite ($NH_4$—$^{80\ to\ 97}Y$) in which 80 weight % to 97 weight % of Na contained in the initial Y-type zeolite (Na—Y) may be ion-exchanged with $NH_4$ is obtained by dispersing the hydrogen type Y-type zeolite obtained above in water at a temperature of 40° C. to 95° C. to prepare a suspension, adding ammonium sulfate thereto, then stifling the suspension at a temperature of 40° C. to 95° C. for 10 minutes to 3 hours, further washing the solid matter with water a temperature of 40° C. to 95° C., next washing it with an ammonium sulfate aqueous solution a temperature of 40° C. to 95° C., subsequently washing it with water a temperature of 40° C. to 80° C. and then drying it at 100° C. to 180° C. for 30 minutes to 30 hours. In some embodiments the final ammonium ion exchange rate is 90% or greater.

The ammonium-exchanged Y zeolite ($NH_4$—$^{80\ to\ 97}Y$) thus obtained may be calcined at 500° C. to 700° C. for 10 minutes to 10 hours in, for example, a saturated vapor atmosphere. Accordingly, an ultra-stable Y-type zeolite (USY) may be prepared having a crystal lattice constant (UD) of 2.430 nm or more and 2.450 nm or less, a specific surface area of 600 m$^2$/g to 900 m$^2$/g, and a molar ratio of SiO$_2$ to Al$_2$O$_3$ of 5:1 to 100:1.

According to one or more methods for producing the catalysts described herein, non-framework aluminum (aluminum atoms which do not form part of the zeolite framework) can be removed from the ultra-stable Y-type zeolite described above which is the raw material in order to obtain the ultra-stable Y-type zeolite having a crystal lattice constant of 2.430 to 2.450 nm. Non-framework aluminum can be removed by, for example, a method of dispersing the ultra-stable Y-type zeolite described above in water at a temperature of 40° C. to 95° C. to prepare a suspension, adding sulfuric acid to the thus-formed suspension and stifling it for 10 minutes to 3 hours while maintaining the temperature at 40° C. to 95° C. to thereby dissolve the non-framework aluminum. After dissolving the non-framework aluminum, the suspension may be filtrated, and a residue on the filter may be washed with purified water at 40° C. to 95° C. and dried at a temperature of 100° C. to 180° C. for 3 to 30 hours, whereby an ultra-stable Y-type zeolite from which the non-framework aluminum is removed can be obtained.

According to one or more methods for producing the catalysts described herein, the ultra-stable Y-type zeolite that is the raw material may be calcined at a temperature of 500° C. to 700° C., in some embodiments at temperatures of 550° C. to 650° C. The time of calcining is typically not critical so long as the targeted framework-substituted zeolite-1 is obtained, for instance, in a range of 30 minutes to 10 hours. If the calcining temperature of the ultra-stable Y-type zeolite is less than 500° C., the framework substitution amount of zirconium atoms and titanium atoms tends to be reduced when carrying out framework substitution treatment by zirconium atoms or titanium atoms at a subsequent step as compared to calcining at 500° C. to 700° C. At calcining temperatures that exceed 700° C., the specific surface area of the ultra-stable Y-type zeolite can be reduced, and a framework substitution amount of zirconium atoms and titanium atoms is thus reduced when carrying out framework substitution treatment by zirconium atoms or titanium atoms at a subsequent step. The calcining atmosphere of the ultra stable Y-type zeolite is, in some embodiments, air.

The calcined ultra-stable Y-type zeolite may be suspended in water having a temperature of 20° C. to 30° C. to form a suspension. With respect to the concentration of the suspension of the ultra-stable Y-type zeolite, the liquid/solid mass ratio is generally in the range of 5:1 to 15:1, and in some embodiments, in the range of 8:1 to 12:1. Next, an inorganic acid or an organic acid may be added thereto so that a pH of the suspension described above is controlled to a range of 1.0 to 2.0, and subsequently a solution containing a zirconium compound is added and admixed. The mixed solution may be neutralized (e.g., to a pH of 7.0 to 7.5), and dried (e.g., at a temperature of 80° C. to 180° C.), whereby the framework-substituted zeolite described above can be obtained. The inorganic acid used can generally be sulfuric acid, nitric acid, hydrochloric acid and the like. In some embodiments, the selected inorganic acid is sulfuric acid or hydrochloric acid. Further, carboxylic acids can suitably be used as the organic acid described above. The quantity of inorganic acid or organic acid may not be critical, so long as the pH of the suspension is controlled in the range of 1.0 to 2.0. For example, a 0.5- to 4.0-fold molar amount, and in some embodiments, a 0.7- to 3.5-fold molar amount based on an amount of Al$_2$O$_3$ in the ultra-stable Y-type zeolite, can be used, although these ranges are not critical.

Suitable zirconium compounds described above include one or more of zirconium sulfate, zirconium nitrate, zirconium chloride and the like. In some embodiments zirconium sulfate and/or zirconium nitrate are selected. The quantity of the zirconium compound added is generally 0.1% to 5% by mass, and in some embodiments 0.2% to 4% by mass, on a zirconium oxide basis with respect to the ultra-stable Y-type zeolite described above. The addition of the zirconium compound in an amount of less than 0.1% by mass fails to improve solid acid characteristics of the zeolite. The addition of the zirconium compound in an amount exceeding 5% by mass tends to cause clogging of pores of the zeolite. An aqueous solution of a zirconium compound prepared by dissolving the zirconium compound in water can be used as the zirconium compound.

A titanium compound can be added to the mixed solution described above. Suitable titanium compounds include one or more of titanium sulfate, titanium acetate, titanium chloride, titanium nitrate, and titanium lactate. In some embodiments titanium sulfate and/or titanium acetate are selected. The quantity of the titanium compound added is generally 0.1% to 5% by mass and, in some embodiments, 0.2% to 4% by mass, on a titanium oxide basis with respect to the ultra stable Y-type zeolite. The addition of the titanium compound in an amount of less than 0.1% by mass results in an ineffective amount of solid acid sites of the zeolite. The addition of the titanium compound in an amount exceeding 5% by mass tends to cause clogging of pores of the zeolite. An aqueous solution of a titanium compound prepared by dissolving the titanium compound in water can be used as the titanium compound.

A pH of the above suspension may be controlled to 1.0 to 2.0 to preventing precipitate from being generated during mixing of the aqueous solution of the zirconium compound and the titanium compound with a suspension of the ultra-stable Y-type zeolite described above.

Mixing of the aqueous solution of the zirconium compound and the titanium compound with a suspension of the ultra-stable Y-type zeolite is, in some embodiments, conducted by gradually adding said aqueous solution to the suspension. After completion of addition of the aqueous solution described above to the suspension, the solution can be mixed by stirring at, for example, room temperature (25° C. to 35° C.) for 3 hours to 5 hours.

Further, after completion of the above-described mixing, the admixed solution may be neutralized by adding an alkali compound such as aqueous ammonia and/or the like, so that a pH thereof is controlled to 7.0 to 7.5, whereby the framework-substituted zeolite described herein is be obtained. The resulting framework-substituted zeolite can be filtered, if desired, washed with water, and dried at 80° C. to 180° C.

Following the production of the framework-substituted zeolite that includes Ti and Zr, the Group 7 metal oxide can be incorporated into the catalyst. In some embodiments, a silica sol comprising $SiO_2$ may be prepared by adding water, glass comprising $SiO_2$, and sulfuric acid simultaneously and continuously. Kaolin, activated alumina, and Group 7 metal oxide may be added to the sol, and the Ti—Zr-USY zeolite slurry may be added. This slurry mixture may be spray-dried to form spherical particles having, for example, an average particle diameter of 30 to 100 micron. The obtained spherical particles may be washed, brought into contact with an aqueous solution of a rare earth metal (RE) chloride for ion exchange, and then dried in an oven.

According to one or more embodiments, an FCC catalyst composition may comprise the disclosed substituted USY zeolites and Group 7 metals. These FCC catalysts may comprise, for example, 15 to 60% by mass, or 20 to 50% by mass, of zeolite, 3.5 to 10% by mass of Group 7 metals, 10 to 30% by mass, or 15 to 25% by mass of inorganic binder as a binding agent, and inorganic oxides other than zeolite as the balance.

In one or more embodiments, the silica based binder and alumina based binder can be used as inorganic binder. The silica based binder can be any one of or two or more of silica sol, water glass (sodium silicate), and silicic acid liquid. For example, silica sol comprising $SiO_2$ at a concentration in the range of 10 to 15% by mass can be prepared by adding water glass comprising $SiO_2$ at a concentration in the range of 12 to 23% by mass and sulfuric acid having a concentration in the range of 20 to 30% by mass simultaneously and continuously. Aluminum-compound binder can be, for example, (a) basic aluminum chloride, (b) aluminum biphosphate, or (c) alumina sol. A solution obtained by dissolving any kind of or two or more kinds of crystallite alumina, such as gibbsite, bayerrite, and boehmite, in an acid solution may be used as the aluminum-compound binder instead. Here, basic aluminum chloride is expressed by Formula 1.

$$[Al_2(OH)_nCl_{6-n}]_m \quad \text{Formula (1)}$$

(where, $0<n<6$ and $1<m<10$, preferably, $4.8<n<5.3$ and $3<m<7$, and the symbol m represents a natural number.) Aluminum biphosphate, also referred to as aluminum dihydrogen phosphate or primary aluminum phosphate, is expressed by $Al(H_2PO_4)_3$. Alumina sol can be produced by, for example, pH adjustment of pseudo-boehmite-type alumina with an acid.

According to embodiments, the inorganic oxides can be, besides kaolin and other clay minerals, activated alumina, porous silica, rare-earth metal compounds, and metal capture agents (metal-trapping agents).

In one or more embodiments, any rare-earth metal oxide may be contained in the catalyst, in the form of $RE_2O_3$, at a content ratio in the range of 0 to 3% by mass. Rare-earth metals used here include cerium (Ce), lanthanum (La), praseodium (Pr), and neodymium (Nd), and catalyst composition may carry any one of or two or more of these as metal oxides.

After USY zeolite preparation, the catalyst may be quasi-equilibrated with steam, for instance, at a temperature of from 600 to 800° C. and for 10 to 20 hours.

In one or more embodiments, fluid catalytic cracking based on a catalyst for fluid catalytic cracking according to the present disclosure can be performed under ordinary conditions for fluid catalytic cracking of hydrocarbon oil. The FCC catalyst for hydrocarbon oil described herein may be charged into a reactor vessel and suitably used for catalytic cracking of hydrocarbon oil according to FCC processes for production of gasoline and/or light olefins including ethylene, propylene and butylenes. For example, a catalytic cracking apparatus may be charged with the FCC catalyst described herein, and hydrocarbon oil having a boiling point above 350° C., in some embodiments in the range of 350° C. to 850° C., can be cracked using fluidized catalytic cracking at a reaction temperature in the range of 450° C. to 700° C., a pressure of 1 to 10 bar, a residence or contact time in the range of 0.1 seconds to 60 seconds, and a catalyst to oil ratio in the range of 2:1 to 30:1.

In some embodiments, a fluidized catalytic cracking unit configured with a riser reactor is provided that operates under conditions that promote formation of light olefins, particularly propylene, and that minimize light olefin-consuming reactions including hydrogen-transfer reactions. FIG. 1 is a simplified schematic illustration of a riser fluidized catalytic cracking unit. FIG. 1 is a suitable cracking unit, but as one skilled in the art would appreciate, the catalysts described herein may be utilized in many varying reactor setups. In FIG. 1, a fluidized catalytic cracking unit 150 includes a riser reactor. Fluidized catalytic cracking unit 150 includes a reactor/separator 160 having a riser portion 161, a reaction zone 163 and a separation zone 165. Fluidized catalytic cracking unit 150 also includes a regeneration vessel 167 for regenerating spent catalyst. A charge 136 is introduced to the reaction zone, in some embodiments accompanied by steam or other suitable gas for atomization of the feed (not shown). The charge 136 is admixed and intimately contacted with an effective quantity of heated fresh or regenerated solid cracking catalyst particles which are conveyed via a conduit 169 from regeneration vessel 167. The feed mixture and the cracking catalyst are contacted under conditions to form a suspension that is introduced into the riser 361. In a continuous process, the mixture of cracking catalyst and hydrocarbon feedstock proceed upward through the riser 161 into reaction zone 163. In riser 161 and reaction zone 163, the hot cracking catalyst particles catalytically crack relatively large hydrocarbon molecules by carbon-carbon bond cleavage.

During the reaction, the cracking catalysts become coked and hence access to the active catalytic sites is limited or nonexistent. Reaction products are separated from the coked catalyst using any suitable configuration known in a fluidized catalytic cracking units, generally referred to as the separation zone 165 in a fluidized catalytic cracking unit 150, for instance, located at the top of the reactor 160 above the reaction zone 163. The separation zone can include any suitable apparatus known to those of ordinary skill in the art such as, for example, cyclones. The reaction product is withdrawn through conduit 171. Catalyst particles containing coke deposits from fluid cracking of the hydrocarbon feedstock pass through a conduit 173 to regeneration zone 167. According to the process herein, since the light solvent feedstock is combined with the heavy feedstock as the feed 136, the solvent to oil ratio in the initial solvent deasphalting/demetallizing process is selected so as to provide sufficient coking of the catalyst to provide the heat balance during regeneration.

Still referring to FIG. 1, in regeneration zone 167, the coked catalyst comes into contact with a stream of oxygen-containing gas, e.g., pure oxygen or air, which enters regeneration zone 167 via a conduit 175. The regeneration zone 167 is operated in a configuration and under conditions that are known in typical a fluidized catalytic cracking operations. For instance, regeneration zone 167 can operate as a fluidized bed to produce regeneration off-gas comprising combustion products which is discharged through a conduit 177. The hot regenerated catalyst is transferred from regeneration zone 167 through conduit 169 to the bottom portion of the riser 161 for admixture with the hydrocarbon feedstock and noted above.

According to embodiments, coke formation is increased due to the incorporation of Group 7 metal oxides on the catalyst. The additional coke may be burned in regeneration zone 167, which produces an increased amount of heat. This heat is needed to drive the main cracking reaction, and as increased coke is present on the catalyst, less or no additional heat is needed as an additive to the process, reducing costs.

In one embodiment, a suitable a fluidized catalytic cracking unit 150 that can be employed using the catalysts described herein can be similar to that described in U.S. Pat. Nos. 7,312,370, 6,538,169, and 5,326,465, which are incorporated herein by reference.

According to various embodiments, the operating conditions for the reactor of a suitable riser fluidized catalytic cracking unit using the catalysts herein may include: reaction temperature of 480° to 650° C., in some embodiments 500° C. to 620° C., and in further embodiments 500° C. to 600° C.; reaction pressure of 1 Kg/cm$^{22}$ to 20 Kg/cm$^2$, in some embodiments of Kg/cm$^2$ to 10 Kg/cm$^2$, in further embodiments of 1 Kg/cm$^2$ to 3 Kg/cm$^2$; contact time (in the reactor) of 0.5 seconds to 10 seconds, in some embodiments of 1 seconds to 5 seconds, in further embodiments of 1 seconds to 2 seconds; and a catalyst to feed ratio of 1:1 to 15:1, in some embodiments of 1:1 to 10:1, and in further embodiments of 8:1 to 20:1.

In some embodiments, a fluidized catalytic cracking unit configured with a downflow reactor is provided that operates under conditions that promote formation of light olefins, particularly propylene, and that minimize light olefin-consuming reactions including hydrogen-transfer reactions. FIG. 2 is a simplified schematic illustration of a downflow fluidized catalytic cracking unit. A fluidized catalytic cracking unit 250 includes a reactor/separator 260 having a reaction zone 262 and a separation zone 264. Fluidized catalytic cracking unit 250 also includes a regeneration zone 266 for regenerating spent catalyst. In particular, a charge 236 is introduced to the reaction zone, in some embodiments accompanied by steam or other suitable gas for atomization of the feed (not shown). An effective quantity of heated fresh or hot regenerated solid cracking catalyst particles from regeneration zone 266 is conveyed to the top of reaction zone 262 also transferred, e.g., through a downwardly directed conduit or pipe 268, commonly referred to as a transfer line or standpipe, to a withdrawal well or hopper (not shown) at the top of reaction zone 262. Hot catalyst flow is typically allowed to stabilize in order to be uniformly directed into the mix zone or feed injection portion of reaction zone 262. The charge 236 is injected into a mixing zone through feed injection nozzles typically situated proximate to the point of introduction of the regenerated catalyst into reaction zone 262. These multiple injection nozzles result in the catalyst and oil mixing thoroughly and uniformly. Once the charge contacts the hot catalyst, cracking reactions occur.

Still referring to FIG. 2, the reaction vapor of hydrocarbon cracked products, unreacted feed and catalyst mixture quickly flows through the remainder of reaction zone 262 and into the rapid separation zone 264 at the bottom portion of reactor/separator 260. Cracked and uncracked hydrocarbons are directed through a conduit or pipe 270 to a conventional product recovery section known in the art to yield fluidized catalytic cracking products light olefins, gasoline and cycle oil, with a maximized propylene yield. If necessary for temperature control, a quench injection can be provided near the bottom of reaction zone 262 immediately before the separation zone 264. This quench injection quickly reduces or stops the cracking reactions and can be utilized for controlling cracking severity.

The reaction temperature, i.e., the outlet temperature of the downflow reactor, can be controlled by opening and closing a catalyst slide valve (not shown) that controls the flow of regenerated catalyst from regeneration zone 266 into the top of reaction zone 262. The heat required for the endothermic cracking reaction is supplied by the regenerated catalyst. By changing the flow rate of the hot regenerated catalyst, the operating severity or cracking conditions can be controlled to produce the desired product slate. A stripper 272 is also provided for separating oil from the catalyst, which is transferred to regeneration zone 266. The catalyst from separation zone 264 flows to the lower section of the stripper 272 that includes a catalyst stripping section into which a suitable stripping gas, such as steam, is introduced through streamline 274. The stripping section is typically provided with several baffles or structured packing (not shown) over which the downwardly flowing catalyst 280 passes counter-currently to the flowing stripping gas. The upwardly flowing stripping gas, which is typically steam, is used to "strip" or remove any additional hydrocarbons that remain in the catalyst pores or between catalyst particles.

The stripped or spent catalyst is transported by lift forces from the combustion air stream 276 through a lift riser of the regeneration zone 264. This spent catalyst, which can also be contacted with additional combustion air, undergoes controlled combustion of any accumulated coke. Flue gases are removed from the regenerator via conduit 278. In the regenerator, the heat produced from the combustion of the by-product coke is transferred to the catalyst raising the temperature required to provide heat for the endothermic cracking reaction in the reaction zone 262. According to the process herein, since the light solvent feedstock is combined with the heavy feedstock as the feed 236, the solvent to oil ratio in the initial solvent deasphalting/demetallizing process is selected so as to provide sufficient coking of the catalyst to provide the heat balance during regeneration.

In one embodiment, a suitable fluidized catalytic cracking unit 250 that can be employed in the process described herein can be similar to those described in U.S. Pat. No. 6,656,346, and US Patent Publication Number 2002/0195373, both of which are incorporated herein by reference. Important properties of downflow reactors include introduction of feed at the top of the reactor with downward flow, shorter residence time as compared to riser reactors, and high catalyst to oil ratio, e.g., in the range of 20:1 to 30:1.

In various embodiments, the operating conditions for the reactor of a suitable propylene production downflow FCC unit may include: reaction temperature of 550° C. to 650° C., in some embodiments 580° C. to 630° C., and in further embodiments 590° C. to 620° C.; reaction pressure of 1 $Kg/cm^2$ to 20 $Kg/cm^2$, in some embodiments of 1 $Kg/cm^2$ to 10 $Kg/cm^2$, in further embodiments of 1 $Kg/cm^2$ to 3 $Kg/cm^2$; contact time (in the reactor) of 0.1 seconds to 30 seconds, in some embodiments 0.1 seconds to 10 seconds, and in further embodiments 0.2 seconds to 0.7 seconds; and a catalyst to feed ratio of 1:1 to 40:1, in some embodiments 1:1 to 30:1, and in further embodiments 10:1 to 30:1.

EXAMPLES

The various aspects of the present disclosure will be further clarified by the following examples. The examples are illustrative in nature and should not be understood to limit the subject matter of the present disclosure.

Example 1—Preparation of a Comparative Catalyst, Catalyst A

First, 50.0 kg of a NaY zeolite (hereinafter, also referred to as "NaY") having a $SiO_2/Al_2O_3$ molar ratio of 5.2, a unit cell dimension (UD) of 2.466 nm, a specific surface area (SA) of 720 $m^2/g$, and a $Na_2O$ content of 13.0% by mass was suspended in 500 liters (L) of water having a temperature of 60° C. Furthermore, 14.0 kg of ammonium sulfate was added to the suspension. The resulting suspension was stirred at 70° C. for 1 hour and filtered. The resulting solid was washed with water. Then the solid was washed with an ammonium sulfate solution of 14.0 kg of ammonium sulfate dissolved in 500 L of water having a temperature of 60° C. The solid was then washed with 500 L of water having a temperature of 60° C. and dried at 130° C. for 20 hours, resulting in 45 kg of a Y zeolite ($NH_4^{65}Y$) in which 65% of sodium (Na) contained in NaY was ion-exchanged with ammonium ion. The content of $Na_2O$ in $NH_4^{65}Y$ was 4.5% by mass.

$NH_4^{65}Y$ 40 kg was fired in a saturated water vapor atmosphere at 670° C. for 1 hour to form a hydrogen-Y zeolite (HY). HY was suspended in 400 L of water having a temperature of 60° C. Then 49.0 kg of ammonium sulfate was added thereto. The resulting mixture was stirred at 90° C. for 1 hour and washed with 200 L of water having a temperature of 60° C. The mixture was then dried at 130° C. for 20 hours, resulting in 37 kg of a Y zeolite ($NH_4^{95}Y$) in which 95% of Na contained in the initial NaY was ion-exchanged with $NH_4$. $NH_4^{95}Y$ 33.0 kg was fired in a saturated water vapor atmosphere at 650° C. for 1 hour, resulting in 15 kg of an ultra-stable Y zeolite (hereinafter, also referred to as "USY(a)") having a $SiO_2/Al_2O_3$ molar ratio of 5.2, a unit cell dimension (UD) of 2.438 nm, a crystallinity of 98%, a specific surface area (SA) of 635 $m^2/g$, and a $Na_2O$ content of 0.60% by mass.

Next, 2.0 kg of the USY(a) was suspended in 20 L of water having a temperature of 25° C. 3.82 kg of 25% sulfuric acid by mass was prepared. Then 106 g of a solution containing 18% zirconium sulfate by mass and 37 g of a solution containing 33% titanium sulfate by mass added. The resulting mixture was stirred for 1 hour at room temperature. The solution was added to suspended USY solution and stirred for 3 hours at room temperature. The mixture was filtered, and the resulting solid was washed with 20 L of water and dried at 130° C. for 20 hours. 1.2 kg of a titanium-zirconium-substituted zeolite (hereinafter, also referred to as "Ti—Zr-USY") was recovered having a $SiO_2/Al_2O_3$ molar ratio of 29.6, a unit cell dimension (UD) of 2.436 nm, a crystallinity of 83%, a specific surface area (SA) of 697 $m^2/g$, a $TiO_2$ content of 0.96% by mass, and a $ZrO_2$ content of 0.49% by mass.

Silica sol comprising $SiO_2$ at a concentration of 12.5% by mass (an example of the silica-based binder) was prepared with a weight of 4000 g by adding 2941 g of water, glass comprising $SiO_2$ at a concentration of 17% by mass, and 1059 g of sulfuric acid having a concentration of 25% by mass simultaneously and continuously. To this silica sol, 950 g of kaolin, and 250 g of activated alumina, weights given on a dry weight basis, were added, and 800 g of a TiZrUSY zeolite slurry prepared with 25% by mass sulfuric acid to have pH of 3.9 was added. This slurry mixture was spray-dried to form spherical particles having an average particle diameter of 60 micron. The obtained spherical particles were washed, brought into contact with an aqueous solution of a rare earth metal (RE) chloride (this solution contained chlorides of cerium and lanthanum) for ion exchange for the content ratio of $RE_2O_3$ to be 1.0% by mass, and then dried in an oven at 135° C. In this way, Catalyst A was produced, having a specific surface area (SA) of 279 $m^2/g$, a $TiO_2$ content of 1.19% by mass, a $ZrO_2$ content of 0.53% by mass, a $Al_2O_3$ content of 23.2% by mass, a rare-earth oxide content of 0.78% by mass.

Example 2—Preparation of a Catalyst Comprising Manganese Oxide, Catalyst B

A Ti—Zr-USY zeolite was produced as described in Example 1. A silica sol comprising $SiO_2$ at a concentration of 12.5% by mass (an example of the silica-based binder) was prepared with a weight of 4000 g by adding 2941 g of water, glass comprising $SiO_2$ at a concentration of 17% by mass, and 1059 g of sulfuric acid having a concentration of 25% by mass simultaneously and continuously. To this silica sol, 815 g of kaolin, 250 g of activated alumina, and 135 g of manganese oxide ($Mn_2O_3$), weights given on a dry weight basis, were added, and 800 g of the Ti—Zr-USY zeolite slurry prepared with 25% by mass sulfuric acid to have pH of 3.9 was added. This slurry mixture was spray-dried to form spherical particles having an average particle diameter of 60 micron. The obtained spherical particles were washed, brought into contact with an aqueous solution of a rare earth metal (RE) chloride (this solution contained chlorides of cerium and lanthanum) for ion exchange for the content ratio of $RE_2O_3$ to be 1.0% by mass, and then dried in an oven at 135° C. In this way, FCC Catalyst B was produced.

Example 3—Catalyst Conditioning

Catalyst A of Example 1 was conditioned as described in this Example. Catalyst A and an olefin additive were conditioned according to ASTM method D4463 (Guide for Metals Free Steam Deactivation of Fresh Fluid Catalytic Cracking Catalyst). Catalyst A and the olefin additive were calcined at 500° C. for 4 hours under a nitrogen flow. Then the temperature was increased to 810° C. at a rate of 5° C. per minute. After the temperature reached 810° C., the nitrogen flow was continued for thirty minutes. Then, the nitrogen flow was stopped and replaced with a steam flow. Water was fed to the preheating zone of the steamer at a rate of three liters per hour. The steam flow continued for six hours at ambient pressure and a temperature of 810° C. Catalyst B of Example 2 was conditioned by the same method.

Example 4—Fluid Catalytic Cracking Reaction Test

Catalyst A of Example 1 and Catalyst B of Example 2 were each tested using an Advanced Cracking Evaluation (ACE) unit. For each catalyst, 7 grams of the catalyst was added to the ACE unit. Additionally, 10 wt. % of a ZSM-5 additive was also used with each catalyst. The catalyst was heated to the reaction temperature of 520° C. with nitrogen gas flowing through the feed injector and from the bottom to maintain fluidization of the catalyst particles. While the reactor temperature was stabilized within ±1° C. of the targeted reaction temperature of 520° C., the hydrocarbon feed was injected to start the catalytic cracking reaction. The feed injection rate was set at 2.4 grams per minute for the test at catalyst/oil ratio of 3.75, and 1.8 grams per minute for a test at catalyst/oil raio of 5.

The feedstock to the ACE unit was a hydrocracking recycle stream, sampled from a two-stage hydrocracking unit. The feedstock properties are summarized in Table 1. Specifically, the feedstock contained few aromatics, indicating that the feedstock included mostly paraffins and naphthenes. Additionally, the feedstock had a low sulfur and nitrogen content.

TABLE 1

| Feedstock Properties. | | |
|---|---|---|
| Property | Unit | Value |
| Density @15° C. | gm/cc | 0.8419 |
| MCR | Wt. % | 0.02 |
| Nitrogen | ppm | <5 |
| Sulfur | ppm | 50 |
| Aromatics | Wt. % | 0.47 |
| Hydrogen | Wt. % | 13.77 |

After being cracked, products exit the ACE unit through a liquid receiver. $C_5^+$ hydrocarbons are condensed and the remaining non-condensable products pass through to a gas receiver. The gaseous product was analyzed using an Agilent Micro GC with four thermal conductivity detectors (TCDs). The liquid product was analyzed using a Varian GC equipped with a flame ionization detector (FID). A simulated distillation was performed on the liquid product according to ASTM D-2887. Three liquid cuts were considered, a gasoline cut (less than 216° C.), a light cycle oil cut (from 216° C. to 343° C.), and a heavy cycle oil (greater than 343° C.).

After stripping is over, the reactor temperature was raised to 650° C. and nitrogen was changed to air for regeneration of catalyst. During regeneration, the flue gas passed through to a $CO_2$ analyzer and the total amount of coke produced during the cracking reaction was calculated from the gas flow rate and the $CO_2$ concentration.

Table 2 shows the catalyst to oil ratio, conversion, and composition of the product stream when Catalyst A was used as the cracking catalyst, and Table 3 shows the catalyst to oil ratio, conversion, and composition of the product stream when Catalyst B was used as the cracking catalyst.

TABLE 2

| Catalyst A | | |
|---|---|---|
| Catalyst Blend | Catalyst A + 10 wt. % ZSM-5 additive | |
| Catalyst/Oil, wt/wt | 3.75 | 5.00 |
| Conversion, wt. % | 88.99 | 90.43 |
| Gasoline, wt. % | 36.64 | 36.82 |
| LCO, wt. % | 7.10 | 6.37 |
| HCO, wt. % | 3.91 | 3.20 |
| Total gas (C4 and lighter), wt. % | 49.16 | 49.91 |
| Dry Gas, wt. % | 3.46 | 3.59 |
| LPG, wt. % | 45.70 | 46.32 |
| Ethylene, wt. % | 2.68 | 2.78 |
| Propylene, wt. % | 16.17 | 16.41 |
| Total Butylene, wt. % | 14.95 | 14.86 |
| Coke, wt. % | 3.19 | 3.70 |

TABLE 3

| Catalyst B | | |
|---|---|---|
| Catalyst Blend | (Catalyst B + 10 wt. % ZSM-5 additive) | |
| Catalyst/Oil, wt./wt. | 3.75 | 5.00 |
| Conversion, wt. % | 89.29 | 90.27 |
| Gasoline, wt. % | 36.67 | 36.66 |
| LCO, wt. % | 6.92 | 6.48 |
| HCO, wt. % | 3.79 | 3.25 |
| Total gas (C4 and lighter), wt. % | 49.05 | 49.46 |
| Dry Gas, wt. % | 3.38 | 3.46 |
| LPG, wt. % | 45.67 | 46.00 |
| Ethylene, wt. % | 2.66 | 2.72 |
| Propylene, wt. % | 16.26 | 16.42 |
| Total Butylene, wt. % | 15.00 | 14.91 |
| Coke, wt. % | 3.57 | 4.16 |

Table 4 shows the difference in yield between Catalyst A and Catalyst B when the conversion of the feedstock is 89.3% by weight. In Table 4 a negative number indicates a reduction of yield due to the manganese oxide additive included in Catalyst B. As shown in Table 4, the inclusion of manganese oxide in Catalyst B results in an increased yield of coke and a decreased yield of dry gas, with minimal changes to the yield of propylene and butylenes.

TABLE 4

Yield Difference Between Catalyst A and Catalyst B

| Product | Change (wt. %) |
| --- | --- |
| Gasoline | −0.01 |
| LCO | −0.03 |
| HCO | 0.03 |
| Total gas (C$_4$ and lighter) | −0.27 |
| Dry gas (C$_2$ and lighter) | −0.11 |
| LPG (C$_3$-C$_4$) | −0.16 |
| Ethylene | −0.04 |
| Propylene | 0.04 |
| Total butylene | 0.07 |
| Coke | 0.27 |

According to a first aspect of the present disclosure, a method for cracking a hydrocarbon oil may include contacting the hydrocarbon oil with a fluidized cracking catalyst comprising an ultra-stable Y-type zeolite in a fluidized catalytic cracking unit to produce light olefins, gasoline fuel, and coke. At least 99 wt. % of the hydrocarbon oil may have a boiling point greater than 350° C. The ultra-stable Y-type zeolite is a framework-substituted zeolite in which a part of aluminum atoms constituting a zeolite framework thereof is substituted with 0.1-5 mass zirconium atoms and 0.1-5 mass % titanium ions on an oxide basis. The fluidized cracking catalyst comprises from 3.5 wt. % to 10 wt. % of one or more Group 7 metal oxides.

A second aspect of the present disclosure may include the first aspect, where the fluidized cracking catalyst comprises from 3.5 wt. % to 10 wt. % of manganese oxide.

A third aspect of the present disclosure may include the first aspect, where the one or more Group 7 metal oxides are chosen from manganese oxide, technetium oxide, rhenium oxide, or bohrium oxide.

A fourth aspect of the present disclosure may include any of the first through third aspects, where coke is formed on the catalyst during cracking, and where the coke heat from burning the coke is sufficient to heat the cracking reaction without further heat sources.

A fifth aspect of the present disclosure may include any of the first through fourth aspects, where the contacting is at a temperature of from 450° C. to 700° C., a pressure of 1 to 10 bars, with a residence time of from 0.1 to 60 seconds, and at a catalyst to oil ratio of from 2:1 to 30:1.

A sixth aspect of the present disclosure may include any of the first through fifth aspects, where the fluidized catalytic cracking unit is a downer reactor.

A seventh aspect of the present disclosure may include any of the first through fifth aspects, where the fluidized catalytic cracking unit is a riser reactor.

An eighth aspect of the present disclosure may include any of the first through seventh aspects, where the fluidized cracking catalyst comprises a mixture of the framework-substituted ultra-stable Y-type zeolite and one or more additional fluidized cracking catalyst materials.

A ninth aspect of the present disclosure may include any of the first through eighth aspects, where the framework-substituted ultra-stable Y-type zeolite has a crystal lattice constant of 2.430 to 2.460 nm, a specific surface area of 600 to 900 m$^2$/g, and a molar ratio of SiO$_2$ to Al$_2$O$_3$ in the range of 5:1 to 100:1.

A tenth aspect of the present disclosure may include any of the first through ninth aspects, where the catalyst comprises from 20% to 50% by mass of zeolite.

An eleventh aspect of the present disclosure may include any of the first through tenth aspects, where the catalyst comprises from 15% to 25% by mass of inorganic binder.

A twelfth aspect of the present disclosure may include the eleventh aspect, where the inorganic binder is silica sol, water glass, or silicic acid liquid.

A thirteenth aspect of the present disclosure may include either the eleventh or twelfth aspects, where the inorganic binder is basic aluminum chloride, aluminum biphosphate, or alumina sol.

A fourteenth aspect of the present disclosure may include any of the eleventh through thirteenth aspects, where the inorganic binder comprises kaolin, clay, activated alumina, porous silica, a rare earth oxide, or a metal trapping agent.

A fifteenth aspect of the present disclosure may include the fourteenth aspect, where the rare earth oxide has formula RE$_2$O$_3$ and is present at a range of 0% to 3% by mass.

A sixteenth aspect of the present disclosure may include the fifteenth aspect, where RE is Ce, La, Pr, or Nd.

A seventeenth aspect of the present disclosure may include any of the first through sixteenth aspects, where the ultra-stable Y-type zeolite has a molar ratio of SiO$_2$ to Al$_2$O$_3$ of from 5:1 to 100:1.

An eighteenth aspect of the present disclosure may include any of the first through seventeenth aspects, where the ultra-stable Y-type zeolite has a molar ratio of SiO$_2$ to Al$_2$O$_3$ of from 10:1 to 80:1.

It will be apparent to a person of ordinary skill in the art that various modifications and variations can be made without departing from the spirit or scope of the present disclosure. Since modifications, combinations, sub-combinations, and variations of the disclosed embodiments incorporating the spirit and substance of the present disclosure may occur to a person of ordinary skill in the art, the scope of the present disclosure should be construed to include everything within the scope of the appended claims and their equivalents.

It is noted that one or more of the following claims utilize the term "where" as a transitional phrase. For the purposes of defining the present disclosure, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated in this disclosure.

Having described the subject matter of the present disclosure in detail and by reference to specific embodiments, it is noted that the various details described in this disclosure should not be taken to imply that these details relate to elements that are essential components of the various embodiments described in this disclosure. Rather, the appended claims should be taken as the sole representation of the breadth of the present disclosure and the corresponding scope of the various embodiments described in this disclosure. Further, it will be apparent that modifications and variations are possible without departing from the scope of the appended claims. More specifically, although some aspects of the present disclosure are identified as particularly advantageous, it is contemplated that the present disclosure is not necessarily limited to these aspects.

What is claimed is:

1. A method for cracking a hydrocarbon oil comprising contacting the hydrocarbon oil with a fluidized cracking catalyst comprising an ultra-stable Y-type zeolite in a fluidized catalytic cracking unit to produce light olefins, gasoline fuel, and coke, wherein:
    at least 99 wt. % of the hydrocarbon oil has a boiling point greater than 350° C.;
    the ultra-stable Y-type zeolite is a framework-substituted zeolite in which a part of aluminum atoms constituting a zeolite framework thereof is substituted with 0.1-5 mass zirconium atoms and 0.1-5 mass % titanium ions on an oxide basis; and
    the fluidized cracking catalyst comprises from 3.5 wt. % to 10 wt. % of one or more Group 7 metal oxides.

2. The method of claim 1, wherein the fluidized cracking catalyst comprises from 3.5 wt. % to 10 wt. % of manganese oxide.

3. The method of claim 1, wherein the one or more Group 7 metal oxides are chosen from manganese oxide, technetium oxide, rhenium oxide, or bohrium oxide.

4. The method of claim 1, wherein coke is formed on the fluidized cracking catalyst during cracking, and wherein the coke heat from burning the coke is sufficient to heat the cracking reaction without further heat sources.

5. The method of claim 1, wherein the contacting is at a temperature of from 450° C. to 700° C., a pressure of 1 to 10 bars, with a residence time of from 0.1 to 60 seconds, and at a catalyst to oil ratio of from 2:1 to 30:1.

6. The method of claim 1, wherein the fluidized catalytic cracking unit is a downer reactor.

7. The method of claim 1, wherein the fluidized catalytic cracking unit is a riser reactor.

8. The method of claim 1, wherein the fluidized cracking catalyst comprises a mixture of the framework-substituted ultra-stable Y-type zeolite and one or more additional fluidized cracking catalyst materials.

9. The method of claim 1, wherein the framework-substituted ultra-stable Y-type zeolite has a crystal lattice constant of 2.430 to 2.460 nm, a specific surface area of 600 to 900 m$^2$/g, and a molar ratio of $SiO_2$ to $Al_2O_3$ in the range of 5:1 to 100:1.

10. The method of claim 1, wherein the fluidized cracking catalyst comprises from 20% to 50% by mass of zeolite.

11. The method of claim 1, wherein the fluidized cracking catalyst comprises from 15% to 25% by mass of inorganic binder.

12. The method of claim 11, wherein the inorganic binder is silica sol, water glass, or silicic acid liquid.

13. The method of claim 11, wherein the inorganic binder is basic aluminum chloride, aluminum biphosphate, or alumina sol.

14. The method of claim 11, wherein the inorganic binder comprises kaolin, clay, activated alumina, porous silica, a rare earth oxide, or a metal trapping agent.

15. The method of claim 14, wherein the rare earth oxide has formula $RE_2O_3$ and is present at a range of 0% to 3% by mass.

16. The method of claim 15, wherein RE is Ce, La, Pr, or Nd.

17. The method of claim 1, wherein the ultra-stable Y-type zeolite has a molar ratio of $SiO_2$ to $Al_2O_3$ of from 5:1 to 100:1.

18. The method of claim 1, wherein the ultra-stable Y-type zeolite has a molar ratio of $SiO_2$ to $Al_2O_3$ of from 10:1 to 80:1.

* * * * *